(12) United States Patent
Rajagopal et al.

(10) Patent No.: US 10,821,053 B2
(45) Date of Patent: Nov. 3, 2020

(54) SYRINGE WITH CONNECTOR

(71) Applicant: Becton, Dickinson and Company, Franklin Lakes, NJ (US)

(72) Inventors: Sambath Kumar Rajagopal, Tamil Nadu (IN); John Di Ubaldi, Jackson, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 215 days.

(21) Appl. No.: 15/724,387

(22) Filed: Oct. 4, 2017

(65) Prior Publication Data

US 2018/0098915 A1 Apr. 12, 2018

Related U.S. Application Data

(60) Provisional application No. 62/405,387, filed on Oct. 7, 2016.

(51) Int. Cl.
*A61J 1/20* (2006.01)
*A61M 5/34* (2006.01)
(Continued)

(52) U.S. Cl.
CPC ........... *A61J 1/2003* (2015.05); *A61J 1/2096* (2013.01); *A61M 5/3134* (2013.01); *A61M 5/34* (2013.01);
(Continued)

(58) Field of Classification Search
CPC ...... A61M 2039/1044; A61M 5/31505; A61M 5/3134; A61M 5/34; A61J 1/2096; A61J 1/2003
(Continued)

(56) References Cited

U.S. PATENT DOCUMENTS 4,220,151 A    9/1980   Whitney
7,794,435 B2   9/2010   Nemoto
(Continued)

FOREIGN PATENT DOCUMENTS

WO    2012/134513 A1    10/2012

OTHER PUBLICATIONS

PCT International Search Report and Written Opinion in PCT/US2017/055534 dated Dec. 18, 2017, 13 pages.

*Primary Examiner* — Brandy S Lee
*Assistant Examiner* — Nidah M Hussain
(74) *Attorney, Agent, or Firm* — Servilla Whitney LLC

(57) ABSTRACT

A syringe comprising a syringe barrel having a distal end, a distal tip, an open proximal end, a barrel sidewall extending between the distal end to the open proximal end and defining a chamber, the barrel sidewall having a barrel sidewall thickness t, the distal end of the syringe barrel including a distal wall is disclosed. The syringe includes a connector integrally formed with and extending distally from the syringe barrel at the distal wall, the connector including a collar disposed coaxially around an elongate tip in fluid communication with the barrel to form a channel between the elongate tip and the collar, the collar including an inside surface, an outside surface and a plurality of ribs extending radially outwardly from the outside surface and separated by spaces, each of the plurality of ribs having a height H and a width W, wherein there is a ratio of the height H to the barrel sidewall thickness t in a range of 0.75 and 1.

19 Claims, 8 Drawing Sheets

(51) Int. Cl.
*A61M 5/31* (2006.01)
*A61M 5/315* (2006.01)
*A61M 39/10* (2006.01)

(52) U.S. Cl.
CPC . *A61M 5/31505* (2013.01); *A61M 2039/1044* (2013.01)

(58) Field of Classification Search
USPC .......................................................... 604/240
See application file for complete search history.

(56) References Cited

U.S. PATENT DOCUMENTS

| | | | |
|---|---|---|---|
| 2003/0073959 A1* | 4/2003 | Koska | A61M 5/348 604/240 |
| 2009/0163859 A1 | 6/2009 | Lloyd et al. | |
| 2011/0077602 A1* | 3/2011 | Yokota | A61M 5/3293 604/239 |
| 2012/0245564 A1 | 9/2012 | Tekeste et al. | |
| 2013/0281983 A1* | 10/2013 | Sherman | A61M 1/06 604/514 |
| 2014/0054295 A1* | 2/2014 | Holtwick | A61M 5/19 220/502 |

* cited by examiner

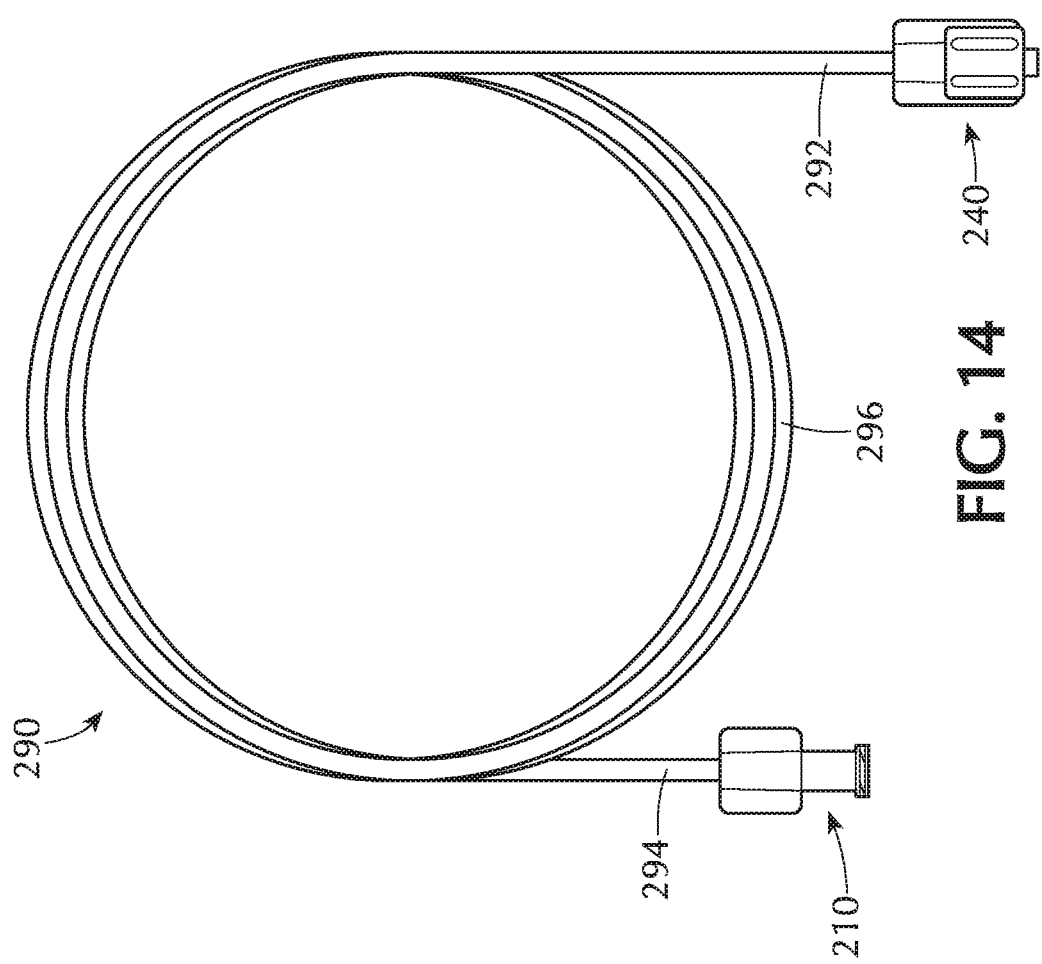

SYRINGE WITH CONNECTOR

CROSS-REFERENCE TO RELATED APPLICATIONS

This application claims priority to U.S. Provisional Application No. 62/405,387, filed Oct. 7, 2016, the entire disclosure of which is hereby incorporated by reference herein.

TECHNICAL FIELD

Aspects of the present disclosure relate to drug delivery devices such as syringes and connectors on the tips of syringes.

BACKGROUND

Connectors used with drug delivery devices typically share a common ISO standard luer connection. A standard male luer tip or standard male connector has specifications as provided by the International Organization for Standardization (ISO) in ISO 594-1:1986 and 594-2:1998, including a 6% taper that increases from the open distal end to the proximal end and an outer cross-sectional diameter at the distal end of the tip measuring between about 0.1545 inches (3.925 mm) and about 0.1570 inches (3.990 mm) for rigid material and between about 0.1545 inches (3.925 mm) and about 0.1585 inches (4.027 mm) for semi-rigid material. A standard female luer hub or standard female luer connector may have a 6% taper that decreases from the open proximal end to the distal end and an inner cross-sectional diameter at the open proximal end measuring between about 0.168 inches (4.270 mm) to about 0.170 inches (4.315 mm). In embodiments of standard female luer connectors that incorporate tabs or lugs for connection to a corresponding male luer lock connector, the outer cross-sectional diameter of the standard female luer connector, including the lugs, is in the range from about 0.307 inches (7.80 mm) to about 0.308 inches (7.83 mm). In embodiments of standard female luer connectors that do not incorporate tabs or lugs for connection to a corresponding male luer lock connector, the outer cross-sectional diameter may be about 0.224 inches (5.700 mm) for rigid connectors and about 0.265 inches (6.730 mm) for semi-rigid connectors, based on the maximum outside diameter of the standard female luer connector at the base of the lugs of ISO 594-2. The minimum length of the standard luer tip and/or the standard luer hub is 0.295 inches (7.500 mm), according to ISO 594-1. As used herein, the phrases "standard male luer connector," "standard male luer tip," "standard female luer hub" and "standard female luer connector" shall refer to connectors having the above dimensions. Connectors that do not have the above dimensions shall be referred to as non-luer connectors.

Standard luer male connectors and standard luer female connectors, collectively referred to herein as standard luer connectors, may be used in intravascular, anesthesia and enteral delivery systems and may include structure that allows a drug delivery device for one system to be to be compatible with other systems. For example, some neuraxial drug delivery systems may use the same type of standard luer connector as the connectors used with other delivery applications, for example, central intravenous catheters, central venous pressure parts, infusion ports, balloon ports, introducer ports, IV luer connectors, peritoneal dialysis catheters, distal port for a pulmonary artery catheter, and many other connectors. An unintended consequence of connecting a drug delivery device for one type of delivery system to connectors for use with other types of delivery systems is that such connection would provide a link between two unrelated systems, i.e., neuraxial to intravenous (IV). Each delivery system is intended to provide unique methods of delivery, with distinctly different purposes and different medications, which the interchangeability of known drug delivery systems can circumvent. Such circumvention can lead to harm and/or serious injury to the patient.

Limiting the use of standard luer connectors for vascular access or systems is one consensus accepted by device manufacturers and regulatory bodies. Accordingly, there has been a need to modify all other devices so they have a different type of connector that cannot physically connect with a standard luer connector or incompatible devices. New proposed standards for small bore connectors, for example ISO 80369-6 for neuraxial applications, have also propelled the need for suitable connectors that do not conform to standard luer connector requirements or non-luer connectors. These new proposed standards include connectors with a 5% taper, instead of a 6% taper that is currently used with standard luer connectors. In addition, the new standards propose connectors with smaller inner and outer cross-sectional diameters and longer lengths than standard luer connectors.

Syringes are also used to deliver fluids for oral delivery of nutrients, storage and delivery of fluid to enteral systems by connecting the syringe to an enteral connection, and intravenous delivery of fluids or medication. Limiting the use of standard luer tips and connectors to use with vascular access systems is one consensus accepted by device manufacturers and regulatory bodies. For example, the recent adoption of ISO 80369-3 provides a uniform standard for small bore connectors for enteral applications, including enteral syringes. However, adoption of the current ISO 80369-3 standard will result in a syringe having connector with a thick syringe collar, and a thick syringe collar may result in high usage of material and reduction in flow of material during molding of enteral syringes. These molding issues can cause mold defects, eventually resulting in production of weak parts. It would be useful to provide syringes having collars that address these molding issues.

SUMMARY

In an embodiment, a syringe is provided, the syringe comprising a syringe barrel having a distal end, a distal tip, an open proximal end, a barrel sidewall extending between the distal end to the open proximal end and defining a chamber, the barrel sidewall having a thickness t, the distal end of the syringe barrel including a distal wall; and a connector integrally formed with and extending distally from the syringe barrel at the distal wall, the connector including a collar disposed coaxially around an elongate tip in fluid communication with the barrel to form a channel between the elongate tip and the collar, the collar including an inside surface, an outside surface and a plurality of ribs extending radially outwardly from the outside surface and separated by spaces, each of the plurality of ribs having a height and a width such that there is a ratio of height H to barrel sidewall thickness t in a range of 075 and 1. In one or more embodiments, the ribs have at least one of a taper and a curve extending in a distal direction from the distal wall. In specific embodiments, the syringe is an enteral syringe, and the connector is configured to meet the requirement under ISO 80369-3, and connection of the tip is prevented with a non-compatible female connector, such as a luer connector that meets the ISO 594:1 or ISO 594:2 standard.

BRIEF DESCRIPTION OF THE DRAWINGS

FIG. 14 is a view of a line set including tubing, which can be used for connection to a syringe according to one or more embodiments.

DETAILED DESCRIPTION

Figure 1:
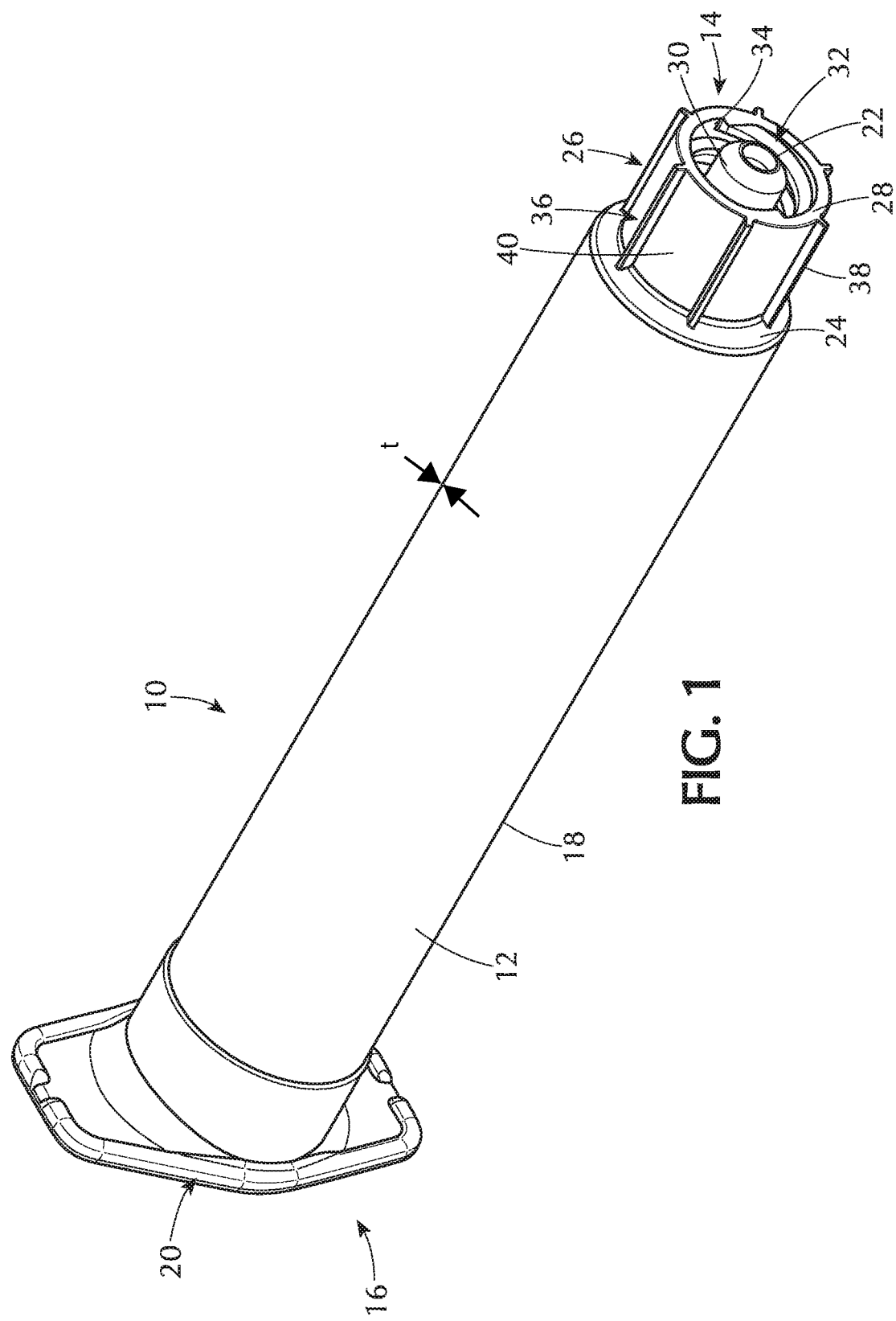
FIG. 1 is a perspective view of syringe having a collar according to one or more embodiments.

Before describing several exemplary embodiments of the disclosure, it is to be understood that the disclosure is not limited to the details of construction or process steps set forth in the following description. The disclosure is capable of other embodiments and of being practiced or being carried out in various ways.

The term "not connectable" with respect to male and female connectors refers to a connector having a shape, size, dimension or structure that prevents connection to another connector. For example, a female luer connector has a shape, size, dimension and/or structure that prevents it from forming a connection with a male non-luer connector and is thus not connectable with respect to the male non-luer connector. Such a female luer connector, however, has a shape, size, dimension and/or structure that permits formation of a connection with a male luer connector and is, thus, connectable with respect to the male luer connector. In another example, a female non-luer connector has a shape, size, dimension and/or structure that prevents formation of a connection with a male luer connector and is, thus, not connectable with respect to the male luer connector. Such a female non-luer connector has a shape, size dimension and/or structure that permits formation of a connection with a male non-luer connector and is thus connectable connector with respect to the male non-luer connector.

As used herein, the term "dimension" shall include the length, diameter or width of a geometric shape or the geometrically shaped components described herein. The term "cross-sectional diameter" shall include the measurement of the longest distance or greatest distance between two points on an edge of a cross-section of an object or component with a circular or non-circular cross-section.

The two points may be located on the inside surface or outside surface of the edge of the cross-section of the object. The cross-sectional diameter of two points located on the inside surface of the edge of the cross-section of the object shall be referred to as the "inside cross-sectional diameter" and the cross-sectional diameter of two points located on the outside surface of the edge of the cross-section of an object shall be referred to as the "outside cross-sectional diameter." It should be recognized that "cross-sectional diameter" of objects having a circular cross-section may be referred to as the "cross-sectional dimension" or "diameter" of the object. The terms "cross-sectional dimension," "cross-sectional diameter" and "diameter" may be used interchangeably for objects having a circular cross-section.

One or more embodiments provide a syringe that has an enteral collar that will enable the syringe meet ISO 80369-3 misconnection requirements. According to one or more embodiments, the syringe can be utilized to draw-up, fill and administer oral medication and fluids as normal oral syringes are currently used, and after the enteral collar is attached the syringe, it will be compliant to ISO 80369-3 and able to be utilized for enteral administration.

One or more embodiments provide a syringe that can be connected to enteral feeding sets and feeding tubes. In the industry, the connection is referred to as ENFit and is compliant to ISO 80369-3. According to one or more embodiments, a syringe is provided that permits the syringe to be connected to enteral tubing and enteral devices such as feeding bags and prevents connection to non-enteral devices, such as intravenous lines, urinary catheters and ventilator tubing. One or more embodiments provide a syringe that is compliant with ENFit devices and ISO 80369-3 and the syringe is not be compatible with a luer connection, thus preventing misadministration of an enteral feeding or medication by the wrong route. Thus, a syringe is provided with a collar that has a connector having a unique enteral-specific design that provides a simple way to reduce the risk of enteral tube feeding misconnections and improve patient safety. Furthermore, the collar does not allow connectivity with any other connector for any other clinical use such as intravenous devices. According to one or more embodiments, a syringe is provided provides an enteral-specific syringe that can be used to administer medicine, flush, hydrate, or bolus feed through the new ENFit feeding tubes and extension sets compliant with ISO 80369-3. One or more embodiments provide a syringe having a collar that does not connect with standard luer connectors that are compliant with ISO Standard 594/1 and 594/2. Thus, an embodiment of the disclosure provides a syringe having a connector with a dimension that is not compatible with standard sized intravenous connectors and ports to keep the two from being inadvertently coupled mechanically.

In one or more embodiments, non-compatible have a shape, size, dimension or structure that does not conform to ISO 594-1:1986 or ISO 594-2:1998. In such embodiments, the non-compatible connector has a shape, size, dimension or structure that prevents it from being characterized or defined as a luer connector as defined above or according ISO 594-1:1986 or ISO 594-2:1998. In one or more specific embodiments, non-compatible connectors may have length and/or cross-sectional diameter that differs from a luer connector as defined above or according ISO 594-1:1986 or ISO 594-2:1998. In a more specific embodiment, the non-compatible connector may have a taper that differs from a luer connector as defined above or according ISO 594-1:

1986 or ISO 594-2:1998. In an even more specific embodiment, the non-compatible connector may have a more gentle taper (for example, 5% taper) than a luer connector as defined above or according ISO 594-1:1986 or ISO 594-2:1998, a cross-sectional diameter that is smaller than a luer connector as defined above or according ISO 594-1:1986 or ISO 594-2:1998 and/or a longer length than a luer connector as defined above or according ISO 594-1:1986 or ISO 594-2:1998.

Embodiments of the disclosure provide a syringe having collar that has a uniform collar wall thickness at the distal tip of the syringe. In one or more embodiments, the syringes described herein have a collar design that prevents molding defects that occur during manufacture of the syringes, and this in turn can reduce the risk of producing weaker collar part while maintaining the ease of injection molding the syringe. In one or more embodiments, it is useful from a quality and manufacturing perspective to maintain a uniform wall thickness on the collar. Syringes having connectors and collars that meet the ISO 80369-3, which are referred to herein as enteral syringes will result in thick collar, and avoiding mold defects and non-uniform wall thickness of the collar can tend to produce weaker syringe collars. According to one or more embodiments, a syringe is provided that has a thick collar and is uniform in thickness, avoids molding defects and can be made reliably in a high volume injection molding environment. One or more embodiments of the syringe designs provided herein provides a syringe manufacturing process permitting enhanced material flow during injection molding of the syringe, particularly at the tip and the collar because the collar of the syringe is designed in such a way that the uniform wall thickness of the collar is achieved. Enhanced material flow, uniform thickness and/or avoiding mold defects can be achieved by varying the number, size, height, thickness, curvature and various other shape, size and density functions of ribs on an outer surface of the syringe collar as described further herein. Thus, embodiments provide an injection molded syringe that can be manufactured using different types of mold to achieve the unique proposed design: conventional molds, CAM action molds, clam shell molds, and collet molds.

Referring now to FIG. 1, a syringe 10 is shown, which comprises a syringe barrel 12 having a distal end 14, a distal tip 22, an open proximal end 16, a barrel sidewall 18 extending between the distal end 14 to the open proximal end 16 and defining a chamber, the barrel sidewall 18 having a barrel sidewall thickness t, the distal end 14 of the syringe barrel 12 including a distal wall 24. The syringe 10 further comprises a connector 26 integrally formed with and extending distally from the syringe barrel 12 at the distal wall 24, the connector 26 including a collar 28 disposed coaxially around an elongate tip 30 in fluid communication with the barrel 12. The collar and the tip form a channel 32 between the elongate tip 30 and the collar 28, and the collar 28 includes an inside surface including threads 34, an outside surface 36 and a plurality of ribs 38 extending radially outwardly from the outside surface 36 and separated by spaces 40. Each of the plurality of ribs 38 includes at least one of a taper and a curve extending in a distal direction from the distal wall. As used herein, "in fluid communication" means that fluid can flow between two or more parts that are in fluid communication. Thus, fluid in the barrel of the syringe can flow though the elongate tip 30, for example, when a plunger (not shown) is advanced in a distal direction in the barrel 12 to expel fluid contained inside the barrel through the elongate tip 30. In the embodiments shown, the collar 28 includes the internal threads 34 providing a female non-luer connector, which can engage a male non-luer connector. In specific embodiments, the enteral syringe 10 having the collar 28 with the threads 34 provides a female connector that provides an ENfit connection that conforms to ISO 80369-3 and is connectable with a male ENfit connector that conforms to ISO 80369-3. According to one or more embodiments, the syringe is an injection molded syringe that is defect free and has a uniform collar wall thickness.

FIGS. 2-13 show various embodiments of connectors that are integrally formed with a syringe such that the number of ribs, size, shape, taper or other features of the ribs are configured to provide a syringe that has a uniform collar wall thickness and does not suffer from manufacturing defects that occur during injection molding of the syringe. As is understood in the art, syringes can be made by an injection molding process through the use of an injection molding machine, raw plastic material, and a mold. The plastic material, e.g., polypropylene, is melted in the injection molding machine and then injected into the mold, where it cools and solidifies into the final part. For ease of illustration, only the connector portion of the syringes are shown in FIGS. 2-13, and each of the connectors shown can be utilized on an enteral syringe as shown in FIG. 1.

Figure 2:
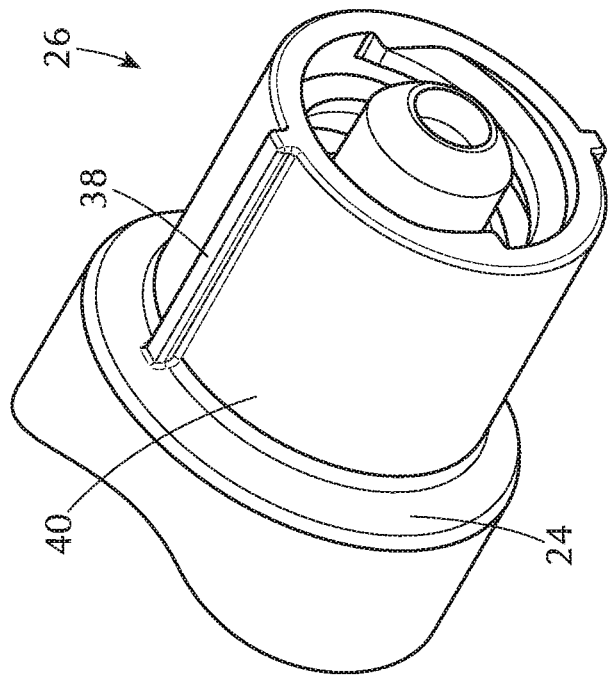
FIG. 2 is a perspective view a collar for a syringe according to an embodiment.
Figure 3:
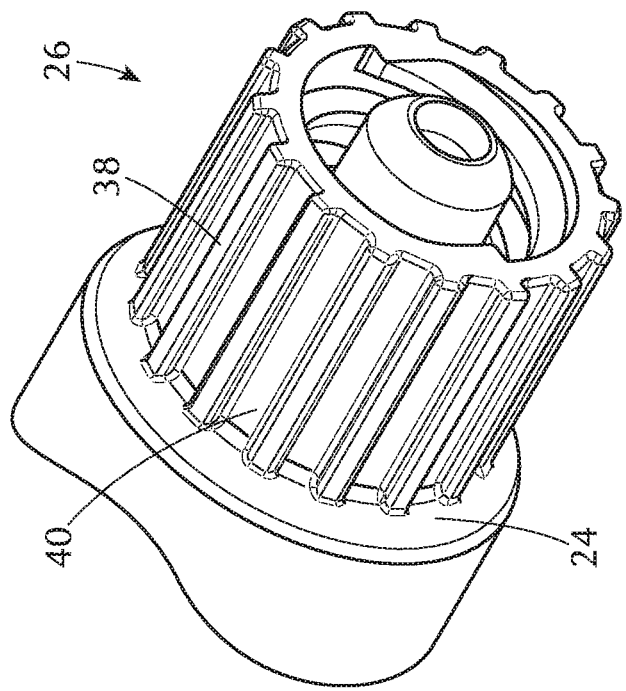
FIG. 3 is a perspective view a collar for a syringe according to an embodiment.

FIG. 2 shows a connector 26 extending from the distal wall 24 of a syringe 10 with a high density or a large number of ribs 38 separated by spaces 40. In the embodiment shown, there are more than six ribs 38 separated by spaces 40. In particular, the connector of FIG. 2 includes sixteen ribs 38 separated by spaces 40. FIG. 3, shows an embodiment with two ribs 38 separated by spaces 40. According to one or more embodiments, there are at least two ribs 38 and two spaces 40. In other embodiments, there are at least six ribs 18 and six spaces 40. In one or more embodiments, there are two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty two or more ribs 38 extending from the outer surface of the connector 26.

Figure 4:
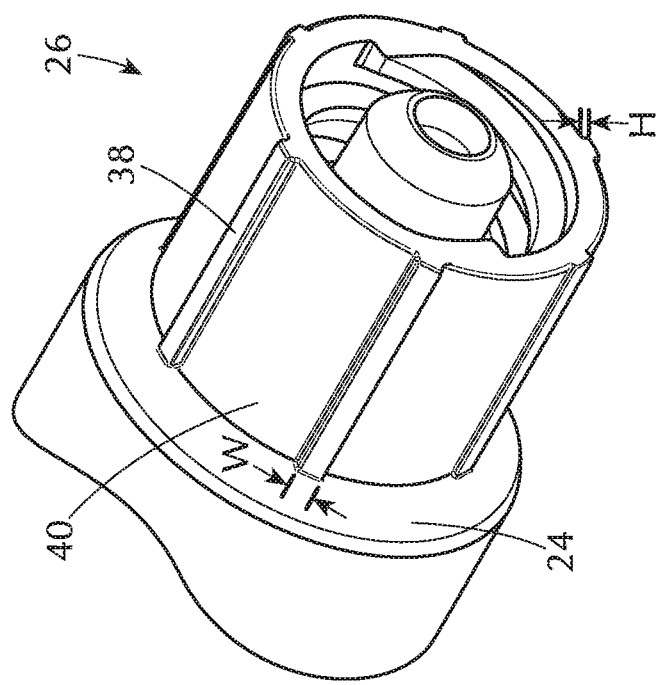
FIG. 4 is a perspective view a collar for a syringe according to an embodiment.
Figure 5:
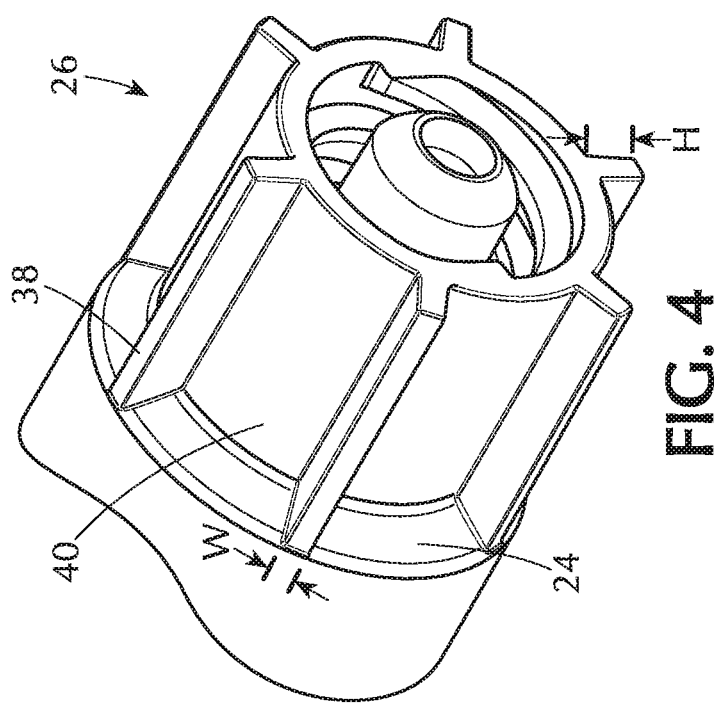
FIG. 5 is a perspective view a collar for a syringe according to an embodiment.
Figure 7:
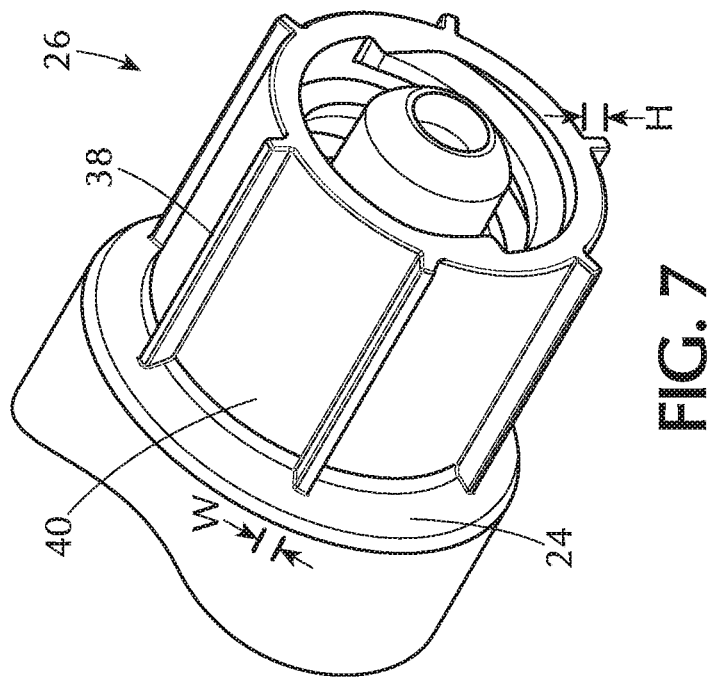
FIG. 7 is a perspective view a collar for a syringe according to an embodiment.
Figure 6:
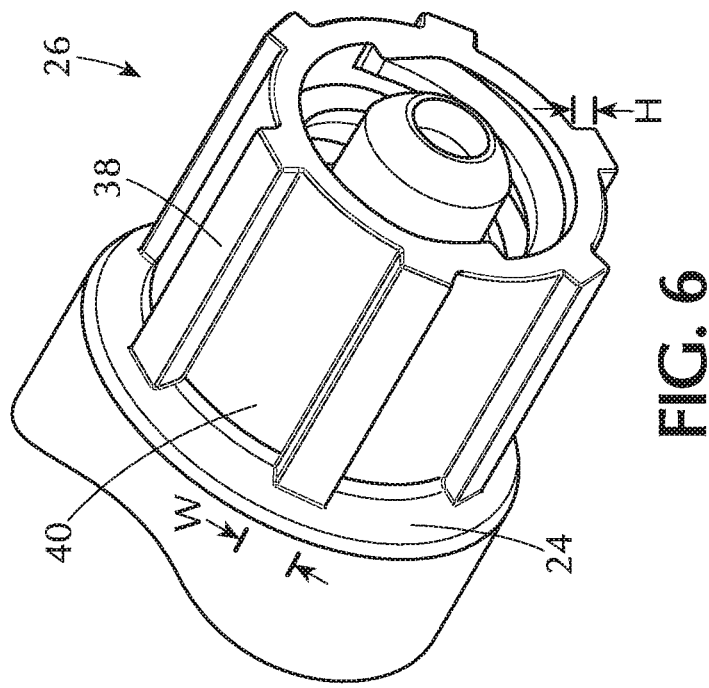
FIG. 6 is a perspective view a collar for a syringe according to an embodiment.

FIG. 4 show an embodiment in which the height H of the ribs 38 is greater than the width W of the ribs 38. In one or more embodiments, there is a ratio of height H to width W of greater than 1.5, 2, 2.5, 3, 3.5, 4, 4.5 or 5. FIG. 5 shows an embodiment in which the height H of the ribs 38 is less than the width W of the ribs 38. In one or more embodiments, there is a ratio of width W to height H of greater than 1.5, 2, 2.5, 3, 3.5, 4, 4.5 or 5. FIG. 6 shows an embodiment in which the width of the ribs 38 is relatively large, and FIG. 7 shows an embodiment in which the width W of the ribs 38 is relatively small. In one or more embodiments, the barrel sidewall thickness t is such that there is a ratio of rib height H to sidewall thickness t (H/t) in a range of 0.75 and 1, and a ratio of rib width W to sidewall thickness t (W/t) in a range of 0.75 and 0.95. In one or more embodiments, the ratio of H to t is in a range of 0.75 and 0.99, or 0.75 and 0.98, or 0.75 and 0.97, or 0.75 and 0.96, or 0.75 and 0.95, or 0.75 and 0.94, or 0.75 and 0.93, or 0.75 and 0.92, or 0.75 and 0.91, or 0.75 and 0.90, or 0.75 and 0.90, or 0.75 and 0.89, or 0.75 and 0.89 or 0.75 and 0.88, or 0.75 and 0.87, or 0.75 and 0.86, or 0.75 and 0.85, or 0.75 and 0.84, or 0.75 and 0.83, or 0.75 and 0.81 or 0.75 and 0.80, while there is a ratio of rib width W to barrel sidewall thickness tin a range of 0.75 and 0.95. In one or more embodiments, the lower end of the range of the ratio of H/t can be 0.80, 0.81, 0.82, 0.83, 0.84 and 0.85. According to an embodiment, a ratio in the aforementioned range, in particular for smaller volume syringes, such as those having a syringe barrel volume of less than 5 ml, for example, 3 ml, the ratio of rib height H to sidewall thickness t (H/t) is in a range of 0.95 and 1, and a ratio of rib width W to barrel sidewall thickness t (W/t) in a range of 0.75 and 0.95, which provides a syringe that has a uniform sidewall thickness and does not suffer from manufacturing defects that occur during injection molding of the syringe. As used herein according to one or more embodiments, "uniform collar wall thickness" refers to a barrel sidewall thickness t variation of less than 0.001 inches or one thousandths.

Figure 9:
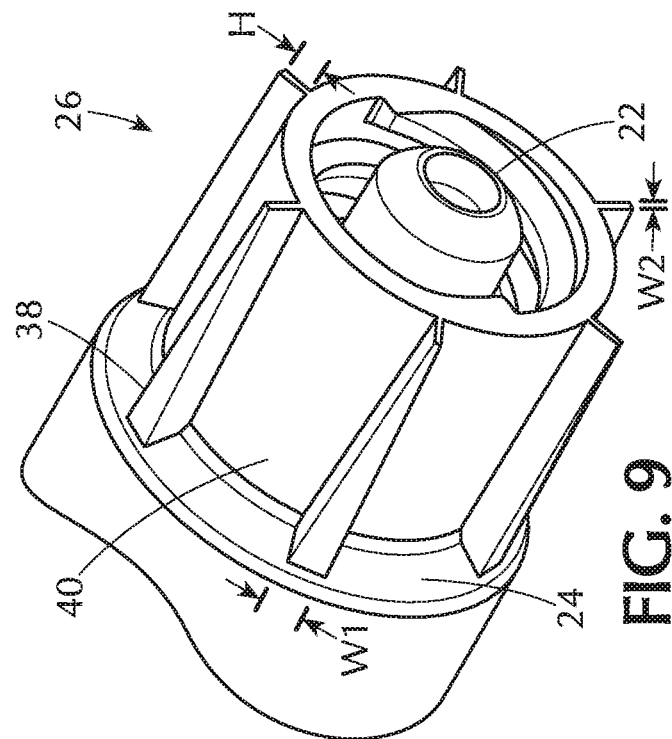
FIG. 9 is a perspective view a collar for a syringe according to an embodiment.
Figure 8:
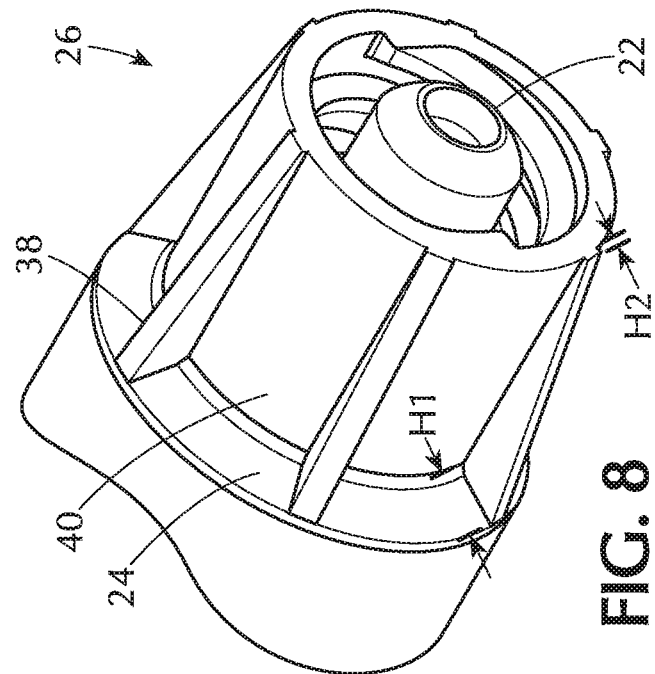
FIG. 8 is a perspective view a collar for a syringe according to an embodiment.

Referring now to FIG. 8, each of the plurality of ribs 38 tapers from the distal wall 24 to the distal tip 22 such that the ribs 38 have a height H1 that is greater at the distal wall 24 than the height H2 at the distal tip 22. Such a configuration results in a tapered rib or a ramped rib 38. FIG. 9 shows an embodiment in which each of the plurality of ribs 38 has a uniform height H and each of the plurality of ribs 38 has a width that tapers such that the width W1 of each of the plurality of ribs is greater at the distal wall 24 than the width W2 at the distal tip 22. This provides a triangular or wedge-shaped rib 38.

Figure 10:
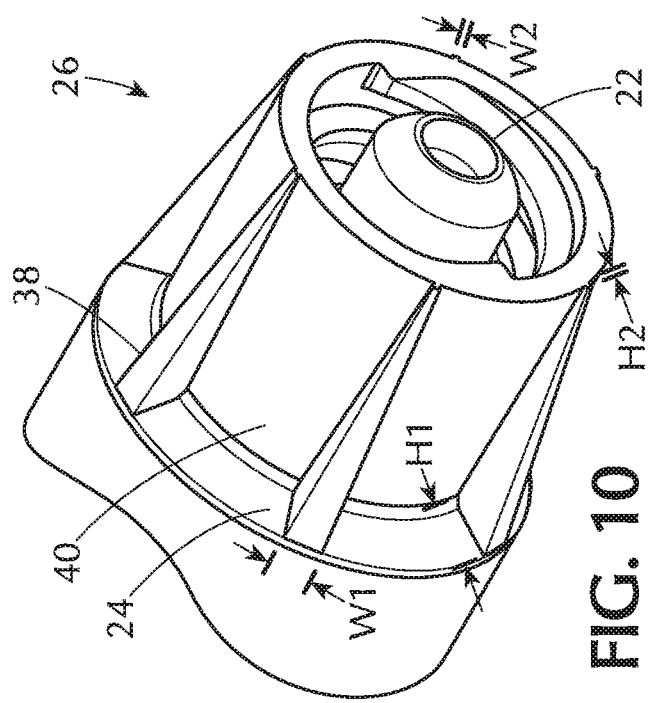
FIG. 10 is a perspective view a collar for a syringe according to an embodiment.

FIG. 10 shows an embodiment in which each of the plurality of ribs 38 tapers from the distal wall 24 to the distal tip 22 such that the ribs 38 have a height H1 that is greater at the distal wall 24 than the height H2 at the distal tip 22, and each of the plurality of ribs 38 has a width that tapers such that the width W1 of each of the plurality of ribs is greater at the distal wall 24 than the width W2 at the distal tip 22. Such a configuration results in a tapered, and triangular or tapered and wedge-shaped rib.

Figure 11:
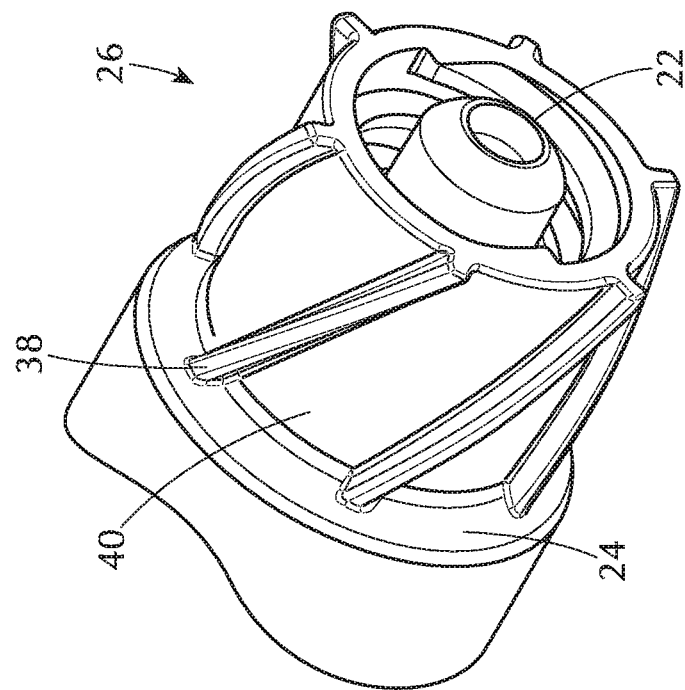
FIG. 11 is a perspective view a collar for a syringe according to an embodiment.
Figure 13:
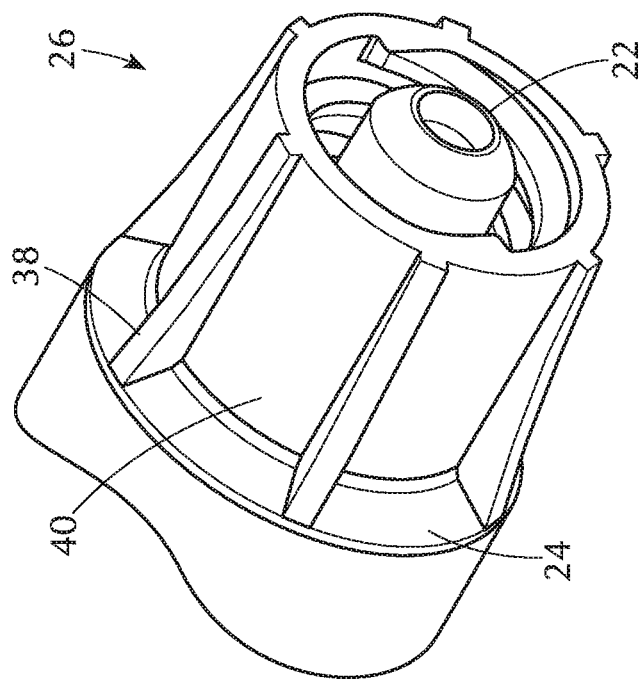
FIG. 13 is a perspective view a collar for a syringe according to an embodiment.
Figure 12:
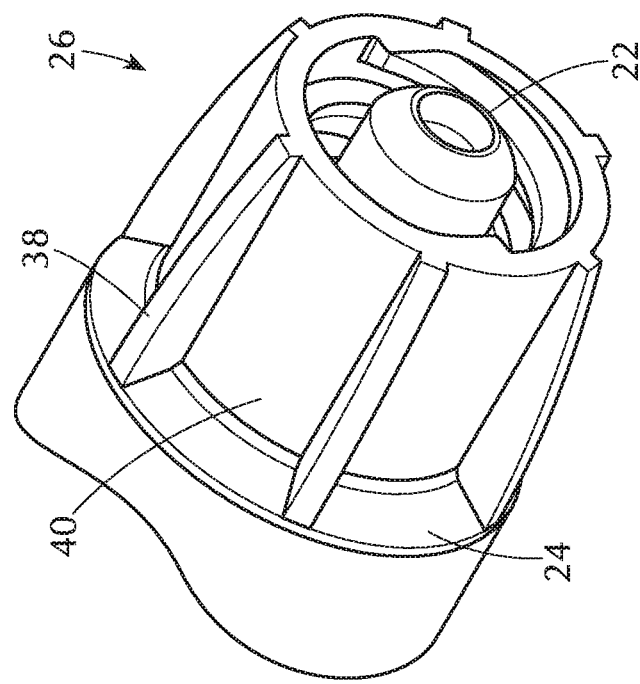
FIG. 12 is a perspective view a collar for a syringe according to an embodiment.

FIG. 11 shows an embodiment in which each of the plurality of ribs 38 curves from the distal wall 24 to the distal tip 22. Specifically, the ribs 38 are curved in a shape of a helix or helical curve from the distal wall 24 to the distal tip 22. FIGS. 12 and 13 each shows an embodiment in which each of the plurality of ribs 38 curves from the distal wall 24 to the distal tip 22 such that the ribs 38 have a height that is greater at the distal wall than at the distal tip. In FIG. 12, each of the plurality of ribs 38 is in a shape of a convex arc with respect to the outside surface. In FIG. 13 each of the plurality of ribs 38 is in a shape of a concave arc with respect to the outside surface.

In one or more embodiments, the syringes described in this disclosure may be connected to a variety of enteral devices, for example, feeding bags and feeding catheters, which is typically accomplished by connecting the enteral collars described herein to flexible tubing. FIG. 14 shows an example of 290 tubing having a male adapter 240 and a female adapter 210 connected to an enteral feeding extension set 290. The male adapter 240 may be disposed at a distal end 292 and the female adapter 210 may be disposed at a proximal end 294. The enteral feeding extension set 290 comprises medical-grade flexible tubing 296. While the tubing 296 is shown coiled in FIG. 14, it will be appreciated that the flexible tubing may be uncoiled and extended the full length of the tubing 296. In use, the female adapter 210 can be connected to the collar 28 in any of the embodiments shown in FIGS. 1-13

The components of the syringes including the enteral collars may be fabricated of a variety of materials suitable for medical and health care applications. For example, the female or male adapters may be fabricated from a medical-grade material, such as, but not limited to, nylon, polypropylene, polycarbonate, polyvinylidene fluoride, acrylonitrile butadiene styrene, and polyvinyl chloride.

Another aspect pertains to a method of manufacturing a syringe comprising injection molding a syringe barrel having a distal end, a distal tip, an open proximal end, a barrel sidewall extending between the distal end to the open proximal end, the barrel sidewall defining a chamber, the distal end of the syringe barrel including a distal wall; a connector integrally formed with and extending distally from the syringe barrel at the distal wall, the connector including a collar disposed coaxially around an elongate tip in fluid communication with the barrel to form a channel between the elongate tip and the collar, the collar including an inside surface, an outside surface and a plurality of ribs extending radially outwardly from the outside surface and separated by spaces, each of the plurality of ribs each of the plurality of ribs having a height H and a width W, wherein there is a ratio of rib height H to the barrel sidewall thickness t (H/t) in a range of 0.75 and 1, and a ratio of rib width W to barrel sidewall thickness t in a range of 0.75 and 0.95. In one or more embodiments, the barrel sidewall thickness t is such that there is a ratio of rib height H to sidewall thickness t in a range of 0.75 and 1, while there is a ratio of rib width W to barrel sidewall thickness t (W/t) in a range of 0.75 and 0.95. In one or more embodiments, the ratio of H to t is in a range of 0.75 and 0.99, or 0.75 and 0.98, or 0.75 and 0.97, or 0.75 and 0.96, or 0.75 and 0.95, or 0.75 and 0.94, or 0.75 and 0.93, or 0.75 and 0.92, or 0.75 and 0.91, or 0.75 and 0.90, or 0.75 and 0.90, or 0.75 and 0.89, or 0.75 and 0.89 or 0.75 and 0.88, or 0.75 and 0.87, or 0.75 and 0.86, or 0.75 and 0.85, or 0.75 and 0.84, or 0.75 and 0.83, or 0.75 and 0.81 or 0.75 and 0.80, while there is a ratio of rib width W to barrel sidewall thickness t in a range of 0.75 and 0.95. In one or more embodiments, the lower end of the range of the ratio of H/t can be 0.80, 0.81, 0.82, 0.83, 0.84 and 0.85. According to an embodiment, the ratio in the aforementioned range, in particular for smaller volume syringes, such as those having a syringe barrel volume of less than 5 ml, for example, 3 ml, the ratio of H to t (H/t) is in a range of 0.75 and 1 and a ratio of rib width W to barrel sidewall thickness t (W/t) in a range of 0.75 and 0.95, which provides a manufacturing process that enables the manufacture of a syringe that has a uniform collar wall thickness and does not suffer from manufacturing defects that occur during injection molding of the syringe. As used herein according to one or more embodiments, "uniform collar wall thickness" refers to a wall thickness variation of less than 0.001 inches or one thousandths of an inch. The injection molding can include flowing injection moldable material into an injection molding device and a mold to form the syringe as described.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A syringe comprising:
   a syringe barrel having a distal end, a distal tip, an open proximal end, a barrel sidewall extending between the distal end to the open proximal end and defining a chamber, the barrel sidewall having a barrel sidewall thickness t, the distal end of the syringe barrel including a distal wall; and
   a connector integrally formed with and extending distally from the syringe barrel at the distal wall, the connector including a collar disposed coaxially around an elongate tip in fluid communication with the syringe barrel to form a channel between the elongate tip and the collar, the collar including an inside surface, an outside surface and a plurality of ribs extending radially outwardly from the outside surface and separated by spaces, each of the plurality of ribs having a height H and a width W, wherein there is a ratio of height H to barrel sidewall thickness t in a range of from 0.75 to 1, and wherein the collar has a collar wall thickness that has a variation of less than 0.001 inches.

2. The syringe of claim 1, wherein each of the plurality of ribs has at least one of a taper and a curve extending in a distal direction from the distal wall, and wherein each of the plurality of ribs tapers from the distal wall to the distal tip such that each of the plurality of ribs has a height or a width that is greater at the distal wall than at the distal tip.

3. The syringe of claim 2, wherein there are at least two ribs and two spaces.

4. The syringe of claim 2, wherein there are at least six ribs and six spaces.

5. The syringe of claim 2, wherein each of the plurality of ribs has a width that tapers such that the width of each of the plurality of ribs is greater at the distal wall than at the distal tip.

6. The syringe of claim 1, wherein each of the plurality of ribs has a uniform height and each of the plurality of ribs has a width that tapers such that the width of each of the plurality of ribs is greater at the distal wall than at the distal tip.

7. The syringe of claim 6, wherein there are at least two ribs and two spaces.

8. The syringe of claim 6, wherein there are at least six ribs and six spaces.

9. The syringe of claim 1, wherein each of the plurality of ribs curves from the distal wall to the distal tip.

10. The syringe of claim 9, wherein there are at least two ribs and two spaces.

11. The syringe of claim 9, wherein there are at least six ribs and six spaces.

12. The syringe of claim 9, wherein the each of the ribs is in a shape of a helical curve from the distal wall to the distal tip.

13. The syringe of claim 12, wherein there are at least two ribs and two spaces.

14. The syringe of claim 12, wherein there are at least six ribs and six spaces.

15. The syringe of claim 1, wherein each of the plurality of ribs curves from the distal wall to the distal tip such that each of the plurality of ribs has a height that is greater at the distal wall than at the distal tip.

16. The syringe of claim 15, wherein there are at least two ribs and two spaces.

17. The syringe of claim 15, wherein there are at least six ribs and six spaces.

18. The syringe of claim 15, wherein each of the plurality of ribs is in a shape of a concave arc with respect to the outside surface.

19. The syringe of claim 15, wherein each of the plurality of ribs is in a shape of a convex arc with respect to the outside surface.

* * * * *